United States Patent [19]
Boss, Jr.

[11] Patent Number: 5,858,390
[45] Date of Patent: Jan. 12, 1999

[54] USE OF AUTOLOGOUS UNDIFFERENTIATED MESENCHYMAL CELLS FOR THE REPAIR OF SKIN AND SOFT TISSUE DEFECTS

[75] Inventor: William K. Boss, Jr., Cedar Grove, N.J.

[73] Assignee: Isolagen Technologies, Inc., West Orange, N.J.

[21] Appl. No.: 926,778

[22] Filed: Sep. 8, 1997

Related U.S. Application Data

[60] Continuation of Ser. No. 660,783, Jun. 6, 1996, Pat. No. 5,665,372, which is a division of Ser. No. 508,773, Jul. 28, 1995, Pat. No. 5,591,444.

[51] Int. Cl.$^6$ .............................. A61F 2/02; A61F 2/10; A61M 31/00
[52] U.S. Cl. .............................. 424/426; 604/51; 623/11; 623/15
[58] Field of Search .............................. 424/426; 604/51; 623/11, 15

[56] References Cited

U.S. PATENT DOCUMENTS

| | | |
|---|---|---|
| 3,949,073 | 4/1976 | Daniels et al. . |
| 4,424,208 | 1/1984 | Wallace et al. . |
| 4,488,911 | 12/1984 | Luck et al. . |
| 4,582,640 | 4/1986 | Smestad et al. . |
| 4,642,117 | 2/1987 | Nguyen et al. . |
| 4,969,912 | 11/1990 | Kelman et al. . |
| 5,002,071 | 3/1991 | Harrell . |
| 5,332,802 | 7/1994 | Kelman et al. . |
| 5,366,498 | 11/1994 | Brannan et al. . |

OTHER PUBLICATIONS

Davies et al., "Autologous Free Dermal Fat Graft. Reconstruction of Facial Contour Defects", Arch Otolaryngol head Neck Surg 121:95–100, 1995.
Spira and Rosen, "Injectable Soft Tissue Substitutes", Clin Plastic Surgery 20:181–189 (1983).
Matton et al., "The History of Injectable Biomaterials and the Biology of Collagen", Aesthetic Plastic Surgery 9:133–140 (1985).
Nicolle et al., "Correction of Age—and Disease–Related Contour Deficiencies of the Face", Aesthetic Plastic Surgery 9:159–162 (1985).
Pieyre, "Collagen Injections: Two Years' Experience", Aesthetic Plastic Surgery 9:153–154 (1985).
DeLustro et al., "Reaction to Injectable Collagen: Results in Animal Models and Clinical Use", Plastic and Reconstructive Surgery 79:581–592 (1987).
"Treatment of Depressed Cutaneous Scars with Gelatin Matrix Implant: A Multicenter Study", J Am Acad Dermatol 16:1155–1162 (1987).
Matti and Nicolle, "Clinical Use of Zyplast in Correction of Age—and Disease–Ralated Contour Deficiences of the Face", Aesthetic Plastic Surgery 14:227–234 (1990).
Ersek, "Transplantation if Purified Autologous Fat: A 3–Year Follow–Up Is Disappointing", Plastic and Reconstructive Surgery 87:219–227 (1991).
Millikan et al., "A 5–Year Safety and Efficacy Evaluation with Fibrel in the Correction of Cutaneous Scars Following One or Two Treatments", J Dermatol Surg Oncol 17:223–229 (1991).
Gonzalez Ulloa, "The Sensuous Lip", Aesthetic Plastic Surgery 16:231–236 (1992).
Hambley and Carruthers, "Microinjection for the Elevation of Depressed Full–Thickness Skin Grafts on the Nose", J Dermatol Surg Oncol 18:963–968 (1992).
Lewis, "The Current Status of Autologous Fat Grafting", Aesthetic Plastic Surgery 17:109–112 (1993).
Gold, "The Fibrel Mechanism of Action Study. A Preliminary Report", J Dermatol Surg Oncol 20:586–590 (1994).
McKinney and Pandya, "Use of Pubic Fat as a Graft for Eyelid Defects", Aesthetic Plastic Surgery 18:383–385 (1994).
Ozgentas et al., "A Comparison of Soft–Tissue Substitutes", Ann Plastic Surgery 33(2):171–177 (1994).
Davies et al., "Autologous Free Dermal Fat Graft. Reconstruction on Facial Contour Defects", Arch Otolaryngol Head Neck Surg 121:95–100 (1995).

*Primary Examiner*—Carlos A. Azpuru
*Attorney, Agent, or Firm*—Pennie & Edmonds LLP

[57] ABSTRACT

The application concerns a method of repairing subcutaneous or dermal tissue in a subject. The method involves the preparation of cultured undifferentiated mesenchymal cells from a specimen obtained from the subject and the injection of the cell preparation to repair the subcutaneous or dermal tissue. The method is applicable to the repair of rhytids, stretch marks, depressed scars and non-traumatic cutaneous depressions as well as to the cosmetic augmentation of the lips.

6 Claims, No Drawings

USE OF AUTOLOGOUS UNDIFFERENTIATED MESENCHYMAL CELLS FOR THE REPAIR OF SKIN AND SOFT TISSUE DEFECTS

This is a continuation of application Ser. No. 08/660,783, filed Jun. 6, 1996, now U.S. Pat. No. 5,665,372, which is a divisional of application Ser. No. 08/508,773, filed Jul. 28, 1995, now U.S. Pat. No. 5,591,444.

1. FIELD OF THE INVENTION

The present invention concerns the repair of skin and soft tissue defects, including wrinkles, in human subjects. More particularly, it concerns a new material for use in non-surgical techniques that augment the volume of the dermis or subcutaneous tissue. By injecting a suspension of autologous cells, the invention provides long-term augmentation of the subadjacent tissue without the disadvantages that accompany the use of presently available materials.

2. BACKGROUND TO THE INVENTION

The injection of a material (an "injectate") into the body, and particularly into the face, to effect an aesthetic result dates to the close of the nineteenth century. For example, the injection of paraffin to correct facial contour defects enjoyed a brief period of acceptance in the years prior to World War I. However, complications and the unsatisfactory nature of the long-term results caused the practice to be abandoned. The availability of injectable silicone gave rise to a virtual repetition of these events beginning in the early 1960's. Specially manufactured "medical grade" silicone solutions, e.g., Dow Corning MDX 4.4011, have been used on an experimental basis in a number of approved test centers in the United States. Complications, such as local and systemic reactions to the silicone, migration of the injectate, and local tissue break down, have limited the use of silicone injections. Although the original proponents of silicone injections have continued their experimental programs with a limited number of subjects, it appears very unlikely that the technique will be adopted by the larger community of surgeons and physicians. Reviewed in Matton, G., et al., 1985, Aesthetic Plastic Surgery 9:133–40; Spira, M. & Rosen, T., 1993, Clin. -Plastic Surgery 20:181–9.

The poor results obtained by the injection of non-biological materials have prompted attempts to use foreign proteins, particularly bovine collagen, as an injectate. Although unprocessed bovine collagen is too immunogenic for injection into humans, the removal by enzymatic degradation of C- and N-terminal peptides of bovine collagen yields a material ("atelocollagen") that can be used in limited quantities if patients are pre-screened to exclude those patients who are immunoreactive. Methods of preparing and using such products are described in U.S. Pat. No. 3,949,073, U.S. Pat. No. 4,424,208 and U.S. Pat. No. 4,488,911. The product has been sold as ZYDERM® brand of atelocollagen in solution at concentrations of 35 mg/ml and 65 mg/ml. Although in widespread world wide use, as of 1987 there more than 200,000 subjects in the United States, the use of ZYDERM is associated by the development of anti-bovine antibodies in about 90% of subjects and with overt immunologic complications in about 1–3% of subjects. DeLustro, F., et al., 1987, Plastic and Reconstructive Surgery 79:581.

Atelocollagen in solution proved to be less than completely satisfactory because the material is, within a period of weeks to months, absorbed by the subject from the site of injection without replacement by host material. Although protocols consisting of repeated injections have been contemplated, such programs are, in practice, limited by the development of immune reactions to the bovine atelocollagen, expense, and by patient resistance. To overcome these limitations, bovine atelocollagen was further processed with glutaraldehyde cross-linking, followed by filtration and shearing by passage through fine mesh. The production and use of this material is described in U.S. Pat. No. 4,582,640 and U.S. Pat. No. 4,642,117. A product produced accordingly is sold as ZYPLASTO® brand of cross-linked bovine atelocollagen. The advantage that cross-linking is intended to provide, an increased resistance to host degradation, is off-set by an increase in viscosity. The increased viscosity and, particularly, the irregular viscosity ("lumpiness") renders the material more difficult to use and even makes it unusable for certain purposes. See, e.g., U.S. Pat. No. 5,366,498.

Moreover, some investigators report that there is no or only marginally increased persistence of ZYPLAST compared to ZYDERM and that the duration of an injections' effects is at most about 4 to 6 months. Matti, B. A. & Nicolle, F. V., 1990, Aesthetic Plastic Surgery 14:227–34; Ozgentas, H. E. et al., 1994, Ann Plastic Surgery 33:171. In the experience of most practitioners there is noticeable absorption after about 4 to 6 weeks.

The limitations imposed by the immunogenicity of bovine collagen products in humans have caused others to consider the preparation of human collagen from placenta, see, e.g., U.S. Pat. No. 5,002,071 and from surgical specimens, see, e.g., U.S. Pat. No. 4,969,912 and U.S. Pat. No. 5,332,802. Further processing of human collagen by cross-linking and other chemical modifications is required because human collagen is subject to the same degradative process as bovine collagen.

Human collagen for injection that is derived entirely from a sample of the subjects own tissue is available and sold under the brand name AUTOLOGEN™. There is no evidence that human collagen injections result in more persistent effects than bovine collagen injections. Further, the use of autologous processed collagen is limited to subjects who have undergone a face-lift procedure, because the starting material for its production is the skin removed during this operation. Clearly then, although autologous processed collagen overcomes the immunogenicity of bovine collagen, it, like bovine collagen, does not provide long-term therapeutic benefits and is limited to patients who have undergone surgery.

Others have injected a mixture of gelatin powder, ε-aminocaproic acid and the subject's plasma ("FIBREL™") as an alternative to atelocollagen for the purpose of augmenting the subadjacent dermis. Multicenter trial, 1987, J. Am. Acad. Dermatol. 16:1155–62.

FIBREL™'s action appears in part to depend upon the induction of a sclerogenic, inflammatory response to augment the soft tissue. Gold, M. H., 1994, J. Dermatologic Surg. Oncol. 20:586–90. Although the reports of FIBREL™ treatments state that they benefit a fraction of patients, see, e.g., Millikan, L., et al., 1991, J. Dermatologic Surg. Oncol. 17:223–29, the results can suffer from lumpiness and a lack of persistence. The use of FIBREL™ has also been limited by the discomfort associated with the injections, and because physicians have found its preparation tedious.

In summary, none of the available non-living injectable materials is wholly satisfactory for the purpose of augmenting the subadjacent dermis and soft tissue.

The inability to obtain long-lasting results with atelocollagen injectates and the problems of using FIBREL™ have prompted some to attempt to obtain and inject (graft) living adipose tissue to augment the subadjacent dermis and soft tissue. Good results in the correction of major defects can be obtained when adipose tissue is surgically removed and reimplanted. See, e.g., McKinney, P. & Pandya, S., 1994 Aesthetic Plastic Surgery 18:383–5; Davies, R. E. et al., 1995 Arch of Otolaryngology—Head & Neck Surgery 121:95–100. However, for repairs that require placement of the graft by injection, the results are decidedly less favorable. Ersek, R. A., 1991, Plastic & Reconstructive Surgery 87:219–27. Thus, even though some beneficial results have been reported, see, e.g., Hambley, R. M. & Carruthers, J. A., 1992, J. Derm. Surgery & Oncol. 18:963–8, the proponents of the method concede that for most practitioners the technique has yielded unsatisfactory results. Lewis, C. M., 1993, Aesthetic Plastic Surgery 17:109–12. Among the problems commonly encountered by physicians and subjects are the unpredictability and lumpiness of the results, which renders the procedure unsuited for treating fine wrinkles, and a period of extreme post-injection swelling, which lasts between 4–6 weeks.

3. SUMMARY OF THE INVENTION

The present invention provides a method of correcting cosmetic and aesthetic defects in the skin of a subject by the injection of a suspension of autologous dermal fibroblasts into the dermis and subcutaneous tissue subadjacent to the defect. Typical defects that can be corrected by this method include rhytids, stretch marks, depressed scars, cutaneous depressions of non-traumatic origin, scaring from acne vulgaris, and hypoplasia of the lip. The cells that are injected, according to the invention, are cells that are histocompatible with the subject and that have been expanded by passage in a cell culture system. In a preferred embodiment, the engrafted cells are dermal fibroblasts, which are derived from the culture of a biopsy specimen taken from the subject.

The invention further provides a method of rendering the passaged dermal fibroblasts substantially free of immunogenic proteins present in the culture medium so that they can be used to correct defects in the skin. The method comprises incubating the expanded fibroblasts for a period of time in protein free medium.

4. DETAILED DESCRIPTION OF THE INVENTION

The present invention is based, in part, on the recognition that the ideal material with which to augment the dermis and subcutaneous tissue subadjacent to a defect would be living cells of the tissue type that is normally present in the dermis. The invention is also based on the recognition that an abundant supply of autologous cells of the desired type can be obtained by culturing a biopsy specimen taken from the subject several weeks prior to injection. The invention is further based on the recognition that, after such a tissue culture expansion, the autologous cells will contain a significant quantity of antigenic proteins, but that the antigenic proteins can be removed, prior to injection into the subject, according to the teaching of the present application.

4.1. METHODS OF OBTAINING AN INJECTABLE CELL SUSPENSION

The invention can be practiced by injecting any undifferentiated mesenchymal cell that can be expanded in culture. In a preferred embodiment, dermal fibroblasts are injected because they can be readily obtained and expanded and because they are one of cell types normally present in the dermis and subadjacent tissue.

A dermal fibroblast culture is initiated from a 2×5 mm full thickness biopsy specimen of the skin. Because of the phenomenon of allograft rejection, which is well known to transplantation surgeons and immunologists, it is essential that the cultured fibroblasts be histocompatible with the host. Histocompatibility can be ensured by obtaining a biopsy of the subject whose dermal defect is to be corrected and culturing the fibroblasts from this specimen.

Before the initiation of the culture, the biopsy is washed repeatedly with antibiotic and antifungal agents. Thereafter, the epidermis and the subcutaneous adipocyte-containing tissue is removed, so that the resultant the culture is substantially free of non-fibroblast cells, and the specimen of dermis is finely divided with scalpel or scissors. The pieces of the specimen are individually placed with a forceps onto the dry surface of a tissue culture flask and allowed to attach for between 5 and 10 minutes before a small amount of medium is slowly added, taking care not to displace the attached tissue fragments. After 24 hours of incubation, the flask is fed with additional medium. When a T-25 flask is used to start the culture the initial amount of medium is 1.5–2.0 ml. The establishment of a cell line from the biopsy specimen ordinarily takes between 2 and 3 weeks, at which time the cells can be removed from the initial culture vessel for expansion.

During the early stages of the culture it is desired that the tissue fragments remain attached to the culture vessel bottom; fragments that detach should be reimplanted into new vessels. The fibroblasts can be stimulated to grow by a brief exposure of the tissue culture to EDTA-trypsin, according to techniques well known to those skilled in the art. The exposure to trypsin is too brief to release the fibroblasts from their attachment to the culture vessel wall. Immediately after the cultures have become established and are approaching confluence, samples of the fibroblasts can be removed for frozen storage. The frozen storage of early rather than late passage fibroblasts is preferred because the number of passages in cell culture of normal human fibroblasts is limited.

The fibroblasts can be frozen in any freezing medium suitable for preserving fibroblasts. A medium consisting of 70% growth medium, 20% (v/v) fetal bovine serum and 10% (v/v) dimethylsulfoxide (DMSO) can be used with good effect. Thawed cells can be used to initiate secondary cultures to obtain suspensions for use in the same subject without the inconvenience of obtaining a second specimen.

Any tissue culture technique that is suitable for the propagation of dermal fibroblasts from biopsy specimens may be used to expand the cells to practice the invention. Techniques well known to those skilled in the art can be found in R. I. Freshney, Ed., ANIMAL CELL CULTURE: A PRACTICAL APPROACH (IRL Press, Oxford England, 1986) and R. I. Freshney, Ed., CULTURE OF ANIMAL CELLS: A MANUAL OF BASIC TECHNIQUES, Alan R. Liss & Co., New York, 1987), which are hereby incorporated by reference.

The medium can be any medium suited for the growth of primary fibroblast cultures. In most instances, the medium is supplement with serum in the amount of between 0.5% and 20% (v/v) to promote growth of the fibroblasts. Higher concentrations of serum promote faster growth of the fibroblasts. In a preferred embodiment the serum is fetal bovine serum, which is added to a final concentration of 10% of medium. The medium for example can be high glucose, DMEM supplemented with 2 mM glutamine, 110 mg/L sodium pyruvate, 10% (v/v) fetal bovine serum and antibiotics "complete medium").

The cells can be passaged into new flasks by trypsinization. For expansion, individual flasks are split 1:3. Triple bottom, T-150 flasks, having a total culture area of 450 cm$^2$ are suitable for the practice of the invention. A triple bottom T-150 can be seeded with about $6 \times 10^6$ cells and has a capacity to yield about $1.8 \times 10^7$ cells. When the capacity of the flask is reached, which typically requires 5–7 days of culture, the growth medium is replaced by serum-free complete medium; thereafter the cells are incubated, i.e., held at between about 30° C. and about 40° C., for at least 6 hours, preferably for greater than 12 hours and most preferably from 16–18 hours at 37° C., in the protein-free medium. The incubation of the cells in serum free medium substantially removes from the cells the proteins that are derived from the fetal bovine serum which, if present, would be immunogenic in the subject and cause an allergic reaction.

At the end of the incubation in serum free medium, the cells are removed from the tissue culture flask by trypsin/EDTA; washed extensively by centrifugation and resuspension; and suspended for injection in an equal volume of injectable isotonic saline. Six triple bottom T-150 flasks, grown to capacity, yields about $10^8$ cells which is sufficient to make up about 1.0 ml of suspension.

Alternatively, the cells can be transported at 4° C. so long as they are injected within 18 hours of the time that the suspension was made. The cells can be suspended in an equal volume of complete medium, except for the absence of phenol red pH indicator, and the replacement of the fetal bovine serum by the subject's serum for such transportation (transport medium). The cells can be aspirated and injected in the transport medium.

The volume of saline or transport medium in which the cells are suspended is not critical. Depending upon such factors as the number of fibroblasts the practitioner desires to inject, the size and number of the defects that are to be treated and the urgency of the subject's desire to obtain the results of treatment, the practitioner can suspend the cells in a larger volume of medium and inject correspondingly fewer cells at each injection site.

4.2. ALTERNATIVE METHOD OF OBTAINING AN INJECTABLE CELL POPULATION IN A VISCOUS SUSPENSION

When the repair of dermal defect requires a large volume of material, the present invention provides an alternative method of preparing an injectable suspension of cells. Examples of such defects include subjects in need of labia oralis augmentation, treatment of nasolabial folds and treatment of subcutaneous defects.

The alternative method is identical to the above-described method until a population of about $1 \times 10^6$ cells is obtained. A plasma clot is formed in the bottom of a 100 mm petri dish, that is treated to have a tissue culture surface, by adding 2 ml of the subject's plasma and 50–100 units of autologous thrombin (typically in 50 $\mu$l) so as to form clot. Cultured dermal fibroblasts, $1 \times 10^6$ cells in 3–5 ml are seeded on the surface of the clot and cultured for a further 7 days in complete medium. At the end of 7 days, the complete medium is exchanged for serum-free medium. A protocol in which the medium is twice removed and replaced with serum-free medium at hourly intervals, and thereafter the cells are incubated a further 14–18 hours in a serum-free medium yields satisfactory results. After the incubation in serum free medium is completed, the clot can be aspirated into a syringe and injected as needed.

In an alternative embodiment of the invention the fibroblasts are not made into a suspension. Rather, the clot is used intact, or cut with a scalpel to a desired shape, and the fibroblast-seeded surface of the clot is applied as a dressing to the subject's dermis after dermal abrasion.

4.3. THE ADMINISTRATION OF THE CELLS TO SUBJECTS

The cell suspensions of the invention can be used to treat dermal defects by use of the same techniques that those skilled in art presently employ to use ZYDERM® and ZYPLAST®. The cell suspension can be used in place of atelocollagen solutions with the advantages set forth as above. Representative teachings concerning the use of injectable material for augmenting the subadjacent dermis and subcutaneous tissue can be found in the surgical literature. Gonzales, U. M., 1992, Aesthetic Plastic Surgery 16:231–4; Nicolle, F. V., 1985, Aesthetic Plastic Surgery 9:159–62; Pieyre, J. M., 1985, Aesthetic Plastic Surgery 9:153–54; which are hereby incorporated by reference in their entirety.

The treatment of fine superficial facial lines, one embodiment of the invention, can be accomplished as follows. The area to be treated is prepped with alcohol and stretched to give a taut surface. A syringe is filled with a cell suspension and fitted with a 30 ga. needle for injection. The needle is inserted into the skin site as superficially as possible; the orientation of the bevel is not critical. An intradermal injection is made by gentle pressure until a slight blanch is seen. Multiple serial injections are made.

In other embodiments the injectate can be placed in the obicularis musculature, to treat hypoplasia of the lip or into the subcutaneous tissue to treat deep subcutaneous defects.

In an alternative embodiment extensive areas of acne scaring can be treated by dermal abrasion to the level of the middle or deep dermis. A fibroblast containing clot is then fashioned so as to cover the abraded surface and applied so that the fibroblast-seeded side of the clot is juxtaposed to the abraded dermal surface. The applied clot is then covered with a surgical dressing such as Xeroform®, Adaptic® or any nonocclusive surgical dressing.

5. SUMMARY OF THE CLINICAL EXPERIENCE

Six patients have undergone treatment of various dermal defects according to the above-described method. The diagnoses were as follows: laugh lines (nasolabial folds), 2 patients; perioral wrinkles, 2 patients; glabellar furrows; depressed scar; lip hypoplasia; and actinic cheek rhytidity.

Each patient was given a forearm test dose of 0.1 ml of the cell suspension. Two patients developed a slight erythema; but there were no other signs of reaction to the injections. Three weeks later therapeutic injections having a total volume of 1.0 ml were made at the site of the dermal defects. Four weeks later in some patients a second therapeutic injection of 1.0 ml was performed. Only in the patient having lip augmentation was a second injection made to repair the same defect; all other patients had only one injection into each treatment area.

The patients had minimal to no erythema and there were no signs of an immediate systemic or local adverse reactions. Each patient was able to work immediately following the injections and in each patient the improvement was immediately noticeable.

There was minimal only discomfort associated with the injections. The discomfort was reported to be less than that associated with bovine atelocollagen injections. The patients expressed their satisfaction with the treatment and their desire to undergo further treatments of other defects. Correction of the dermal defects has been noted by friends and associates of the patients who had no knowledge of the treatments. There are no visible sequelae of the treatment of the skin, although some evidence of the treatment can be detected by palpation.

There have been no delayed local or systemic adverse reactions during a six month post-injection trial period. None of the patients have developed lumps, irregularities or unevenness. Most significantly, the therapeutic effects of the injections have shown no diminution during the period of observation, which has extended to more than 6 months from the time of injection, during which time, a bovine atelocollagen injection would have been expected to be absorbed. Rather, the therapeutic effects in some patients available for long-term follow-up showed benefits that increased with time. The late onset of long-term improvements indicates that the injected fibroblasts are metabolically active and lay down additional extra-cellular matrix at the site of injection.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited references are, hereby, incorporated by reference.

I claim:

1. A method for the long-term augmentation of subcutaneous or dermal tissue in a human subject which comprises:

a) providing a suspension of autologous, passaged undifferentiated mesenchymal cells;

b) identifying a defect that is susceptible to amelioration by augmentation of the subadjacent subcutaneous or dermal tissue; and c) injecting an effective volume of the suspension into the subadjacent tissue so that the tissue is augmented.

2. The method of claim 1, wherein the defect is a rhytid, stretch mark, a depressed scar, a cutaneous depression of non-traumatic origin or an under-development of the lip.

3. The method of claim 1, wherein the suspension further comprises human fibrin in an amount effective to form an injectable gel.

4. The method of claim 3, wherein the injectable gel is comprised of thrombin-activated homologous plasma.

5. The method of claim 1, which further comprises the steps of:

a) biopsying a tissue of the subject;

b) passaging the undifferentiated mesenchymal cells from the tissue biopsy in a culture medium comprising between 0.5% and 20% non-human serum, so as to provide undifferentiated mesenchymal cells substantially free of other cells;

c) incubating the passaged cells in a serum-free medium for at least 6 hours at between about 30° C. and about 40° C.; and d) exposing the incubated cells to a proteolytic enzyme so as to suspend the cells.

6. The method of claim 1, wherein the undifferentiated mesenchymal cells are dermal fibroblasts.

* * * * *